Figure 2:

United States Patent [19]

Drillien et al.

[11] Patent Number: 5,180,675
[45] Date of Patent: Jan. 19, 1993

[54] RECOMBINANT FOWLPOX VIRUS

[75] Inventors: Robert Drillien, Strasbourg; Danièle Spehner, Eckbolsheim, both of France

[73] Assignee: Transgene, S. A., Courbevoie Cedex, France

[21] Appl. No.: 264,493

[22] Filed: Oct. 28, 1988

[30] Foreign Application Priority Data

Oct. 29, 1987 [FR] France .................. 87 15001
Jun. 20, 1988 [FR] France .................. 88 08226

[51] Int. Cl.$^5$ ............. C12N 7/01; C12N 15/86; A61K 39/275
[52] U.S. Cl. ................. 435/235.1; 424/89; 435/236; 435/320.1; 935/32
[58] Field of Search ............ 435/235.1, 236, 69.1, 435/172.3, 320.1, 240.2; 424/89, 93; 935/22, 23, 32, 34, 57, 65, 70

[56] References Cited

U.S. PATENT DOCUMENTS

| 3,429,965 | 2/1969 | Gelenczei et al. | 424/89 |
| 4,603,112 | 7/1986 | Paoletti et al. | 435/235.1 |
| 5,093,258 | 3/1982 | Cohen et al. | 435/235.1 |

FOREIGN PATENT DOCUMENTS

| 580059 | 12/1988 | Australia . |
| 0162757 | 11/1985 | European Pat. Off. . |
| 0227414 | 7/1987 | European Pat. Off. . |
| 0284416 | 9/1988 | European Pat. Off. . |
| 0338807 | 10/1989 | European Pat. Off. . |
| 8600528 | 1/1986 | PCT Int'l Appl. . |
| 8607609 | 12/1986 | PCT Int'l Appl. . |
| 8605806 | 10/1986 | World Int. Prop. O. . |
| 8802022 | 3/1988 | World Int. Prop. O. . |
| 8907644 | 8/1989 | World Int. Prop. O. . |
| 8912684 | 12/1989 | World Int. Prop. O. . |

OTHER PUBLICATIONS

Panicali, D. et al. 1983, Proc. Natl. Acad. Sci. USA, vol. 80, pp. 5364–5368.
Perkus, M. E. et al. 1985, Science vol. 229 pp. 981–984.
Binns, M. M. et al. 1988, J. Gen. Virol. vol. 69 pp. 1275–1283.
Hanggi, M. et al. 1986, EMBO Journal vol. 5 pp. 1071–1076.
Schnitzlien, W. M. et al. 1988, Virus Research vol. 10 pp. 65–76.
Spehner, D. et al. 1990, J. Virol. vol. 64 pp. 527–533.
Boyle, D. B. et al. 1988, Virus Research vol. 10 p. 343–356.
Mackett, M. et al. 1986, J. Gen. Virol. vol. 67 pp. 2067–2082.
Binns, M. M. et al. 1986, Isr. J. Vet. Med. vol. 42 pp. 124–127.
Drillien, R. et al. 1987, Virology vol. 160 pp. 203–209.
Boyle, D. B. et al. 1986, J. Gen. Virol. vol. 67 pp. 1591–1600.
Taylor, J. et al. 1988, UCLA Symp. Mol. Cell. Biol, New Ser. vol. 84 pp. 321–234.
Taylor, J., et al. 1988, Vaccine vol. 6 pp. 497–503.
Taylor, J. et al. 1988, Vaccine vol. 6 pp. 504–508.
Morita, M., et al. 1987, Vaccine vol. 5, pp. 65–70, "Recombinant vaccinia virus LC16mO or LC16m8 that expresses hepatitis B . . . ".
Lathe et al, Nature 37, 326 (1987) Apr. 30–May 6 No. 6116, "Tumour Prevention and Rejection with Recombinant Vaccinia" pp. 878–880.
Panicali et al, Gene 47 (1986) 193–199 "Vaccinia virus vectors utilizing the beta-galactosidase assay for rapid selection . . . ".

Primary Examiner—Richard A. Schwartz
Assistant Examiner—Mary E. Mosher
Attorney, Agent, or Firm—Cushman, Darby & Cushman

[57] ABSTRACT

Recombinant fowlpox virus, derived from an attenuated strain, which has integrated in a non-coding intergenic region of its genome a DNA sequence coding for a heterologous protein.

2 Claims, 5 Drawing Sheets

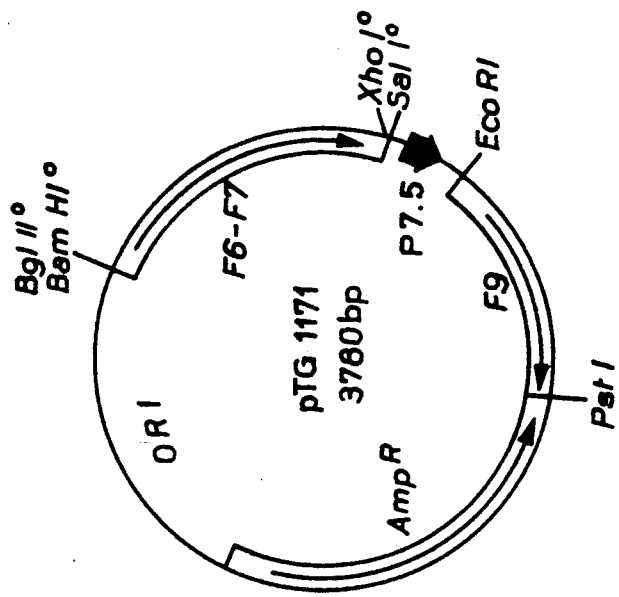
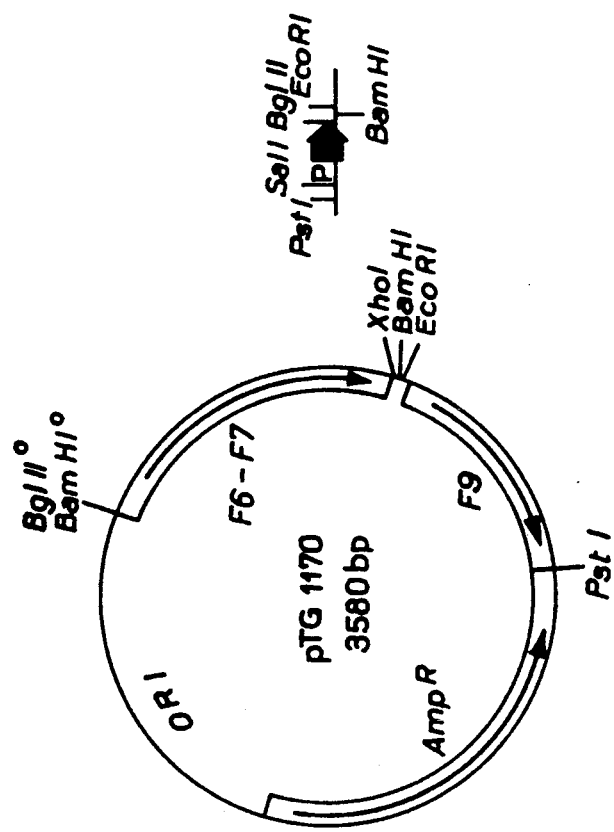
FIG.1

FIG_3

RECOMBINANT FOWLPOX VIRUS

The present invention relates to recombinant viruses of fowl variola, commonly known as fowlpox, and to their applications to the preparations of vaccines or of proteins which are useful to the metabolism of poultry.

Viruses of the Poxviridae family, to which the fowlpox virus belongs, are double-stranded DNA viruses which multiply in the cytoplasm of the cells and code for a large part of the enzymatic machinery necessary to their replication.

Purified viral DNA is not infectious, because enzymes associated with the viral particle are necessary for initiating its expression and its replication. However, it can participate in recombination events with the DNA of an infectious virus introduced into the same cell. This discovery (Sam and Dumbell, 1981) is the basis of the development of vectors for the cloning and expression of foreign genes, derived from vaccinia virus (Mackett et al. 1982; Panicali and Paoletti, 1982). Live recombinant vaccinia viruses have made it possible to express foreign antigens and, thus, to obtain immunizations against different viral or parasitic diseases (Smith et al. 1983; Panicali et al. 1983; Kieny et al. 1984; Chakrabarti et al. 1986; Hu et al. 1986; Kieny et al. 1986).

Although recent publications have mentioned the use of fowlpox as a vector (Brown, 1985 and Taylor et al., 1987), no experimental result has been published to date, and the molecular biology of the fowlpox virus has not yet been subjected to detailed studies, in contrast to the biology of the vaccinia virus, which has been well studied (see review by Moss, 1985).

The subject of the present invention is the use of the fowlpox virus by way of a vector for the expression of heterologous proteins.

More specifically, the subject of the invention is a recombinant fowlpox virus which is derived from an attenuated strain, that is to say rendered artificially non-pathogenic, and which contains, in a non-essential portion of its genome, a DNA sequence coding for all or part of a heterologous protein, as well as the elements providing for its expression by the fowlpox virus in a suitable cell.

In one of its aspects, the invention relates to the preparation of a vaccine, especially a vaccine which protects poultry against at least one of the viral diseases eases which can affect it. In this case, the heterologous protein is a protein that induces an immune response against a heterologous virus. Among heterologous viruses of interest, Newcastle disease virus, infectious bronchitis virus and Marek's disease virus may be mentioned.

The present invention relates especially to the use of the fowlpox virus for the preparation of vaccines against Morbilliviruses, and its subject is hence a fowlpox virus in which the DNA sequence codes for a protein that induces an immune response against a Morbillivirus.

Among viruses belonging to the Morbillivirus family, measles virus, Carre's disease virus, rinderpest virus and the virus of little ruminant's pest (peste de petits ruminants) may be mentioned.

Study of the different Morbilviruses has enable the immunological relationships between the surface proteins of the measles virus and those of the other Morbilliviruses to be demonstrated, as well as sequence homologies between the DNAs coding for some of these proteins. These similarities make it possible to envisage the use of measles virus antigens for vaccination against Carre's disease, rinderpest and little ruminant's pest (peste des petits ruminants). It is also possible to foresee the use of the surface antigens originating from each of the Morbilliviruses in a homologous or heterologous vaccination system.

The surface protein, such as the hemagglutinating protein (HA) and the fusion protein (F) are more especially advantageous, but other structural proteins, such as the nucleoprotein (NP) could be used. The corresponding DNA sequences can code for the full-length protein or alternatively for fragments that are sufficient for inducing in vitro the synthesis of antibodies neutralizing the Morbillivirus.

It is also possible to foresee the use of a DNA sequence coding for several proteins or several fragments of the latter.

In another of its aspects, the invention relates to the production in vivo, in poultry, of a factor participating in the metabolism of the latter such as, for example, a growth hormone or a factor that induces the latter (such as GRF). In this case, the heterologous protein is the said factor and the fowlpox virus contains the elements providing for its expression in vivo. To obtain this production, a fowlpox virus according to the invention, which contains the gene coding for this factor, is administered to the animal, the virus being live.

Finally, the invention enables proteins of industrial or therapeutic importance to be prepared in cell culture, in particular in avian cells, in vitro and also in vivo in animals.

The expression of a sequence coding for a foreign protein by a poxvirus, and in particular by the fowlpox virus, necessarily involves the following three stages:

1) the coding sequence must be aligned with a poxvirus promoter and be inserted in a non-essential segment of the DNA of the fowlpox virus, cloned into a suitable bacterial plasmid;
2) the DNA sequences of the fowlpox virus situated on each side of the coding sequence must permit homologous recombinations to take place between the plasmid and the viral genome in a receptor cell; a double recombination leads to a transfer of the DNA insert from the plasmid into the viral genome in which it will be propagated and expressed;
3) the DNA sequence integrated in the recombinant fowlpox genome must be expressed in a suitable cell that withstands the multiplication of the virus.

It has been stated above that the insertion of the foreign DNA must be carried out in a non-essential portion of the fowlpox virus genome, that is to say a portion which does not prevent its replication. The introduction of the foreign gene into the TK gene, as in recombinant vaccinia viruses, might have been envisaged. However, since the starting strain is an attenuated strain, it may be feared that the impairment of a function useful for its replication might constitute an excessively large handicap and strongly decrease its immunogenic power, and thereby that of the foreign antigen expressed by the recombinant virus. For this reason, according to a characteristic of the present invention, the foreign DNA sequence is introduced into a non-coding intergenic region of the fowlpox virus. This intergenic region is preferably situated between ORFs 7 and 9 of the 1.3-kpb HindIII fragment of the genome, according to Drillien et al. (1987).

The invention also relates to the eukaryotic cell cultures which are infected with the recombinant virus according to the invention, and which permit its replication. Among cells which may be envisaged, avian cells may be mentioned, in particular.

The subject of the invention is also vaccines obtained from these recombinant viruses, in the form of live or inactivated viruses. The methods of preparation of the vaccines are known to those versed in the art, and will not be recalled here.

The invention also relates to live recombinant viruses whose administration can make possible the production in vivo, during viral multiplication, of a factor which is useful to the metabolism of poultry.

Finally, the invention relates to DNA sequences containing at least one gene which is heterologous to the fowlpox virus, under the control of a poxvirus promoter, flanked on each side by the 3' end of ORF 7 and the 5' end of ORF 9, as well as to plasmids carrying these DNA sequences.

These plasmids are useful, in particular, in the context of a process for obtaining a recombinant virus according to the invention, wherein a culture of competent cells is transfected with the DNA of a plasmid according to the invention, the said culture having been infected beforehand with a fowlpox virus optionally containing a selection element.

Other characteristics and advantages of the invention will become apparent in the desired description which follows. The following 4 figures illustrate the examples:

FIG. 1: diagrammatic representation of plasmid pTG1170 and of the insert carrying the 7.5 kd promoter which has been introduced into the polylinker to give pTG1171.

FIG. 2: photograph of a dish of a chick fibroblast culture showing the plaques of recombinant fowlpox virus expressing β-galactosidase, and which appear colored blue in the presence of X-Gal.

Figure 3:
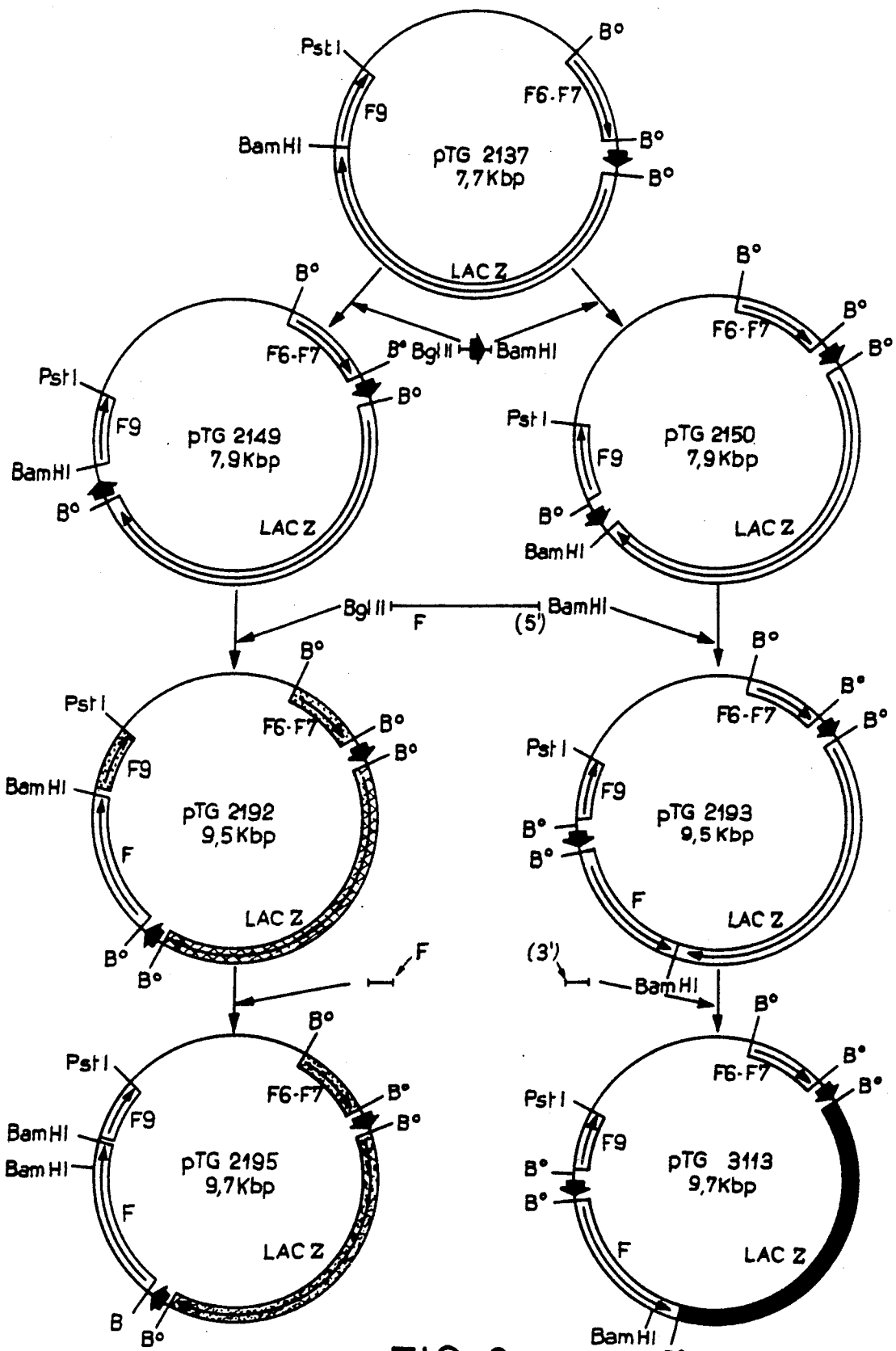

FIG. 3: construction of two vectors permitting the transfer of the gene coding for the F protein of the measles virus into the fowlpox virus genome.

The DNA sequence of the fowlpox genome are represented by double-lined arcs of the circle labelled according to the reading frames which they contain: either $F_6$–$F_7$, or $F_9$. The single-lined arc of circle represents the bacterial vector pPolyII. The P7.5 promoter is shown schematically by a thick arrow indicating the direction of transcription. The genes coding for β-galactosidase of $E.\ coli$ and the F protein of the measles virus are labelled Lac Z and F measles, respectively, and their normal reading direction is the same as that of the P7.5 promoter situated downstream from each gene. The sites designated B° correspond to the point of a ligation between a BglII site and a BamHI site.

Figure 4:
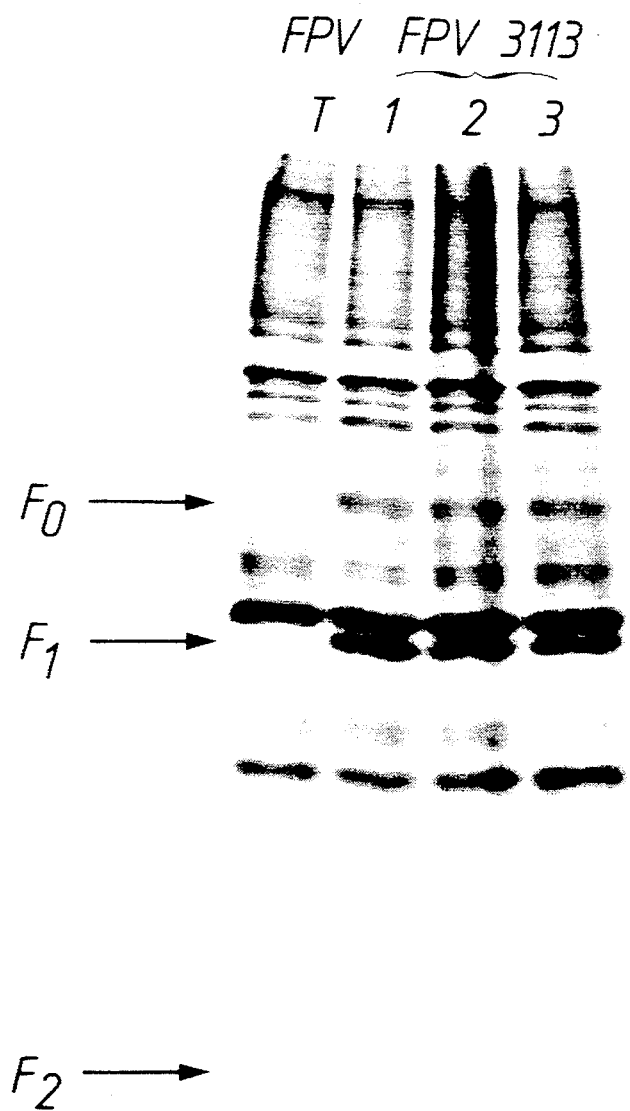

FIG. 4: Demonstration of the synthesis of the F protein of the measles virus in cells infected with the virus FPV3113.

The proteins of chick cells infected with the wild-type strain of fowlpox (lane labelled T) or three isolates of the recombinant strain FPV3113 (lanes labelled 1, 2 and 3) were immunoprecipitated with a guinea pig antimeasles serum and then analyzed by polyacrylamide gel electrophoresis. The autoradiograph of the dried gel is shown. The different forms of the F protein ($F_0$, $F_1$, $F_2$) are designated by arrows.

Figure 5:
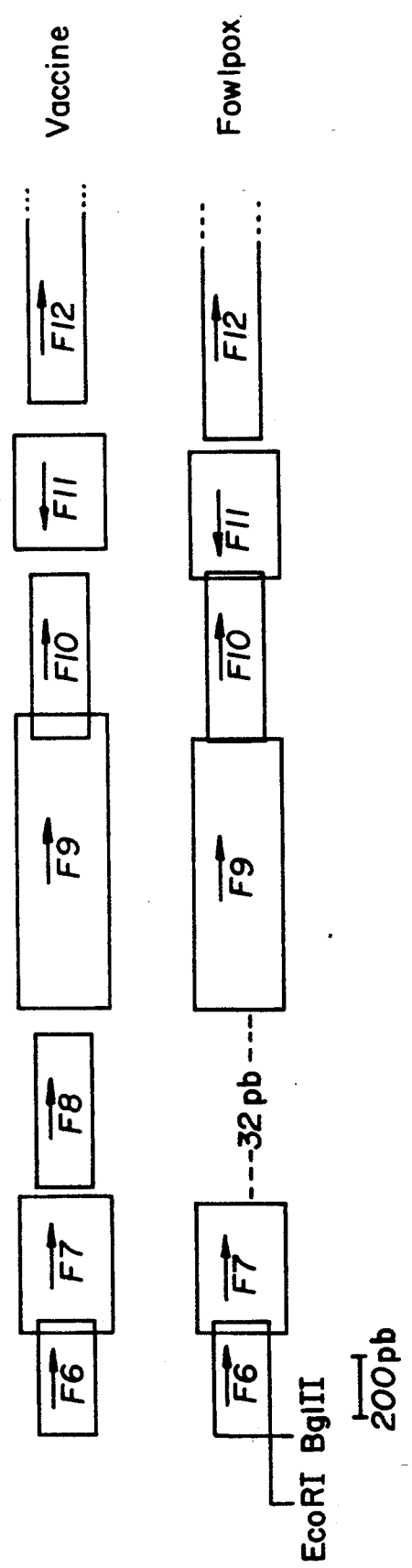

FIG. 5: DNA fragment of fowlpox possessing substantial homology with DNA of the vaccinia virus.

EXAMPLE 1

Selection and characterization of temperature-sensitive (ts) mutants of the fowlpox virus.

A vaccinal strain of the virus of fowl variola, or fowlpox, for example the vaccine produced by Salsbury Laboratories (Poxine ®, Laboratoire Salsbury, 56 Rue Delprier, 37000 TOURS, France), is used.

The multiplication of the virus is measured at 3 temperatures:

|  | Titer after 6 days: |
| --- | --- |
| 33° C. | 4.1 × 10⁵ pfu/ml |
| 37° C. | 4.1 × 10⁵ pfu/ml |
| 39.5° C. | 4.2 × 10⁵ pfu/ml |

The non-mutated virus multiplies as efficiently at all 3 temperatures.

A stock of virus, cloned and amplified at 39.5° C., is treated with nitrosoguanidine at a concentration of 10 or 20 μg/ml. After this mutagenic treatment, the virus is plated, at a dilution suitable for obtaining well isolated plaques, on chick embryo fibroblast cultures. The cultures are incubated at 33° C. (permissibe temperature) for 6 to 7 days, and then stained with neutral red to reveal the viral plaques.

The cultures are then incubated at 39.5° C. (restrictive temperature) for 2 days. The plaques whose size has not increased are considered to be temperature-sensitive. The viruses of a few plaques are removed and amplified at 33° C., and then retitrated at 33° and 39.5° C. to confirm their ts nature. The following nature shows the titers obtained at the 2 temperatures.

| Titration at: | 33° C. | 39.5° C. |
| --- | --- | --- |
| Control fowlpox virus | 1 × 10⁵ | 1 × 10⁵ pfu/ml |
| mutant ts1 | 2 × 10⁵ | <10 pfu/ml |
| mutant ts11 | 2 × 10⁵ | <10 pfu/ml |
| mutant ts24 | 2 × 10⁵ | <10 pfu/ml |

EXAMPLE 2

Perfecting the conditions for recombination between ts mutated viruses and purified DNA of non-mutated virus.

Under restrictive condtions, the ts mutants no longer multiply.

The purified DNA of viruses of the Poxviridae family is not infectious.

If the introduction of a ts virus and a purified DNA into the same cell gives rise to a multiplication of viruses, the latter result from a complementation or an in vivo recombination between the 2 genomes.

Lawns of chick embryo fibroblasts are infected with the ts viruses (4×10⁴ pfu/10⁶ cells). After 1 hour's adsorption, the cultures are replenished with fresh medium and incubated for 2 hours at a permissive temperature (33°–37° C.).

The medium is then removed and the purified DNA of the non-mutated virus is then adsorbed in the form of a calcium phosphate precipitate (1 μg of DNA in 5 μl of buffer for 4 culture dishes).

After 1 hour's adsorption, the cultures are replenished with fresh medium and incubated for 2 hours at a non-permissive temperature (39.5° C.), and they are then subjected to a glycerol (10%) shock.

The cultures are then incubated again for 5 days at 39.5° C.

The viral plaques are counted, half of them directly on the dishes in which the manipulation has been performed, and half of them after amplification (that is to say after freezing of the first dishes followed by a second multiplication cycle).

| | Number of viral plaques | | | |
|---|---|---|---|---|
| | without amplification | | after amplification | |
| | without DNA | +DNA | without DNA | +DNA |
| ts1 | 0 | 15 | 10 | $3 \times 10^4$ |
| ts11 | 0 | 2 | 10 | $1 \times 10^4$ |
| ts24 | 0 | 3 | 10 | $1 \times 10^4$ |

The experiment shows that the purified DNA of wild-type fowlpox virus can be reactivated by ts mutants to give and infectious progeny.

The mutant ts1 was adopted for the following experiments.

EXAMPLE 3

Construction of a vector intended for the transfer of heterologous DNA into the fowlpox virus.

To transfer a foreign DNA sequence into the genome of a virus, this sequence must be integrated in the midst of intact sequences of the virus so as to permit a double homologous recombination to take place.

The foreign DNA must be inserted in a non-essential region of the virus so as not to prevent multiplication of the latter.

A vector was constructed to promote the insertion of a foreign DNA into a non-coding integenic region of the fowlpox virus.

a) Insertion of a DNA fragment of fowlpox into a bacterial plasmid: construction of pTG1170.

A DNA fragment of fowlpox possessing substantial homology with the DNA of the vaccinia virus has been described by Drillien et al. (1987).

This fragment (homologous with the HindIII J fragment of the vaccinia virus) carries 5 open reading frame (ORF) sequences, and differs from vaccinia by the absence of a F8 gene, which is replaced by a non-coding intergenic region of 32 base pairs (see FIG. 5).

This intergenic region was chosen as the insertion site for the foreign DNA.

A large DNA fragment which surrounds this region was recovered for use as a homologous sequence permitting recombination and integration to take place in the fowlpox viral genome. This fragment was obtained after digestion with EcoRI and PstI. The EcoRI site is situated upstream from ORF6 and the PstI site is situated in ORF9 )see diagram above). The EcoRI-PstI fragment was integrated in a vector M13TG131 (Kieny et al. 1983), to give M13TG188.

The introduction into M13 enables a localized mutagenesis to be performed, in order to introduce recognition sites for restriction enzymes which will permit the insertion of foreign DNA.

3 sites were created, XhoI, BamHI and EcoRI, in the 32-bp intergenic region, using the following synthetic oligonucelotide:

5'TTAAAAAGGAATTGACTCGAGGGATC-
CGAATTCAAGAAAATATTTAT 3'

The construction carrying the synthetic insert is referred to as M13TG195. The presence of the restriction sites was verified with the corresponding enzymes.

The mutated fowlpox DNA sequence was recovered from M13TG195 in the form of a BglII-PstI fragment (the BglII site is situated at the beginning of ORF6, Drillien et al. 1987), and introduced into a cloning vector derived from pML2 carrying a synthetic adaptor containing several restriction sites, POLYII described by Lathe et al. (1987).

The insertion of the BglII-PstI fragment of fowlpox into the vector POLYII, opened with BamHI and PstI, gives plasmid pTG1170, which is shown diagrammatically in FIG. 1.

b) Insertion of a poxvirus promoter into the vector pTG1170.

To obtain the expression of a foreign gene by a poxvirus, it is necessary to place this gene under the control of a poxvirus promoter.

Initially, a well characterized promoter of the vaccinia virus, the promoter of the 7.5K protein gene, referred to for short as the "7.5K promoter", was used. The 7.5K promoter of the vaccinia virus, recovered in the form of a SalI-EcoRI fragment from a vector M13TG7.5K described by Kieny et al. (1984), was introduced into the vector pTG1170.

This promoter sequence was introduced between the XhoI and EcoRI sites of the synthetic adaptor of pTG1170 (see FIG. 1).

The resulting construction, pTG1171, hence carries the 7.5K promoter inserted between ORF6-7and ORF9 of fowlpox, with a BamHI site (provided by the P7.5K sequence) and an EcoRI site immediately downstream.

EXAMPLE 4

Insertion of a foreign gene into the vector pTG1171.

A model gene was used for demonstrating the usefulness of the vector and of the system for selection of fowlpox virus recombinants: the β-galactosidase gene of E. coli. This gene was chosen because its efficient expression may be readily detected by adding X-Gal (5-bromo-4-chloro-3-indolyl-β-D-galactopyranoside), which generates a blue coloration under the action of β-galactosidase.

The lacZ gene coding for β-galactosidase of E. coli may be recovered, for example, from plasmid pCH110 (Hall et al. 1983). The lacZ gene was excised with BamHI and HindIII and inserted into the cloning vector POLYII (mentioned above), the taken up in the form of a BglII-BamHI fragment and inserted in pTG1171 opened with BamHI and treated with phosphatase.

The construction carrying the lacZ gene downstream from 7.5K promoter is referred to as pTG1177.

EXAMPLE 5

Expression of a foreign gene by a recombinant fowlpox virus.

The DNA of plasmid pTG1177 (100 ng/$10^6$ cells) was transfected into chick embryo cells infected beforehand with fowlpox virus ts1, according to the protocol described in Example 5.

After 5 days' incubation at 39.5° C., the recombinant viruses are harvested after lysing the cells by freezing.

The viruses are titrated on chick embryo fibroblast cultures, under agar medium. After 5 days, the viral plaques are visualized with X-Gal (solution containing 30 mg/ml, diluted to 1/100 in PBS medium + 1% agarose).

The viral plaques stain blue, thereby indicating the presence of functional β-galactosidase.

EXAMPLE 6

Construction of a second vector intended for the transfer of heterologous DNA into the fowlpox virus.

a) Another vector enabling heterologous DNA to be transferred into the fowlpox virus was constructed by retaining a larger intergenic region between ORFs F7 and F9. To achieve this objective, a first localized mutagenesis was performed on the phage M13TG188 (described in Example 3) with the following synthetic oligonucleotide

5'
AACAACCTAATATCACTATAG-
GATCCTTGTTAAAAAGGAAT 3'

This gives the phage M13TG2123, and results in the introduction of a BamHI site into the 3' coding portion of ORF F7. A second mutageneis was then performed on M13TG2123 with the following oligonucleotide

5'
CCTAATATCACTACTGAAGCGCAAC-
TAGGATCCTTGTTAA 3'

In the resulting phage, M13TG2125, the intergenic distance between ORF F7 and ORF F9 is increased by about fifteen nucleotides, and the codons situated on the 3' side of ORF F7 are replaced by equivalent codons, coding for the same amino acids. The mutated fowlpox DNA sequence was recovered from M13TG2125 in the form of a BglII-PstI fragment, and introduced into the vector POLYII as in Example 3, to generate plasmid pTG2134.

b) Insertion of a poxvirus promoter into the vector pTG2134.

The promoter of the 7.5K protein gene of the vaccinia virus, recovered in the form of a BglII-BamHI fragment of a vector M13TG2119 (derived from M13TG7.5K described in Example 3), was inserted in the BamHI site of plasmid pTG2134. This gave rise to two vectors, pTG2135 and pTG2136, which differed from one another in the orientation of the promoter. In plasmid pTG2135, the promoter is oriented in the same direction as ORF F7 and F9, while in plasmid pTG2136, the orientation is reversed.

EXAMPLE 7

Insertion of a foreign gene into the vectors pTG2135 and pTG2136.

As in Example 4, the β-galactosidase gene, in the form of a BglII-BamHI fragment, was inserted into the vectors pTG2135 and pTG2136, opened beforehand with BamHI and treated with phosphatase. These manipulations gave rise to the vector pTG2137, in which the β-galactosidase gene is oriented in the same direction as the genes of ORFs F7 and F9, and to the vector pTG2138, in which the orientation of the β-galactosidase gene is reversed.

The DNA of pTG2137 was transfected into chick embryo cells infected with the fowlpox virus ts1, as in Example 5.

Plaques of recombinant viruses are observed after 5 days, and they stain blue after adding X-Gal.

EXAMPLE 8

Insertion of a foreign gene different from the β-galactosidase gene in cells into the fowlpox genome and expression in cells infected with recombinant fowlpox viruses.

A. Construction of the recombinant viruses

The construction of a vector (pTG2137) which makes it possible to transfer the β-galactosidase gene into the fowlpox genome and to recognize the recombinant viruses by virtue of the blue color of the fowlpox plaques in the presence of a chromogenic substrate (X-Gal) has been described in the main patent. It is possible, in addition, to select for the integration of a second gene in the fowlpox genome without the latter imparting a new, readily detectable phenotype to the virus. This is illustrated for the case of the gene coding for the F protein of the measles virus.

The stages are as follows:

Initially, a second P7.5 promoter was added to plasmid pTG2137 in order to provide for the transcription of a second gene independent of β-galactosidase. The P7.5 promoter was obtained in the form of a BglII-BamHI fragment excised from the phage M13TG2119 described previously. The P7.5 promoter was integrated downstream from the β-gal gene in the BamHI site of the vector pTG2137, either in the same orientation as the first P7.5 promoter to give plasmid pTG2149, or in the opposite orientation to give plasmid pTG2150.

The cDNA coding for the F gene of the measles virus was then inserted downstream from the new p7.5 promoter in the two vectors pTG2149 and pTG2150. First, the cDNA coding for the N-terminal portion of the F protein was excised by cutting pTG1172 with the enzymes BglII and BamHI, and the fragment obtained was inserted in the BamHI site of pTG2149 or pTG2150 so as to comply with the correct direction of transcription of the F gene relative to the p7.5 promoter and give rise, respectively to plasmids pTG2192 and pTG2193.

The cDNA coding for the C-terminal portion of the F gene was then isolated from pTG1173 by cutting with the enzyme BamHI, and the fragment added to pGT2192, cut beforehand with the same enzyme so as to re-form an intact F gene. The C-terminal portion of the F gene in plasmid pTG1173 contains a poly(A) region which had been deleted in the phage M13TG2143. The latter provided the C-terminal portion of the F gene in the form of a BglII-BamHI fragment added to plasmid pTG2193 cut with BamHI. The plasmid formed during the above ligation is referred to as pTG3113.

Plasmids pTG2195 and pTG3113 hence each contain the complete F gene of the measles virus under the control of the P7.5 promoter, either in the same orientation as the first P7.5 promoter which governs the expression of the β-galactosidase gene (pTG2195), or in the opposite orientation. The combination of clonings carried out which generated recombinant plasmids is summarized in FIG. 3.

The recombinant plasmids pTG2195 and pTG3113 were used to transfer the β-galactosidase gene and the F protein gene into the fowlpox virus genome according to the techniques described in Examples 2 and 5.

Plaques of recombinant fowlpox viruses designated FPV2195 and FPV3113 were identified by virtue of the blue color in the presence of X-gal. The virus present in the plaques was taken up, amplified by infection of chick embryo cells and then plated again. Blue plaques were identified and the above procedure repeated.

This successive cloning technique showed that the virus FPV3113, after being freed from the non-recombinant virus which initially contaminated it, possesses a stable β-galactosidase phenotype. In contrast, the virus FPV2195, subjected to the same successive cloning cycles, proves unstable, that is to say an isolated blue plaque gives approximately 2% of colorless plaques, incapable of coding for β-galactosidase. The virus FPV2195 isolated at the beginning hence tends to segregate the β-gal gene while retaining the gene which codes for the F protein; the resulting virus is referred to as FPV2195 β-gal−. The loss of the β-gal gene probably takes place following inter- or intramolecular recombination events between the two P7.5 promoters placed in direct repetition with respect to the β-gal gene. This method has the advantage of permitting the initial selection for integration of a chosen gene (in this case the F gene) by virtue of the β-gal marker which is physically combined with it, then the removal of the marker by a natural recombination mechanism of the virus, and finally the possible reuse of the marker for the insertion of another gene or of the same in another region of the genome.

B. Expression of the F protein in cells infected with FPV2195 β-gal- and FPV3113

Chick embryo cells were infected with approximately 1 pfu per cell of FPV3113, FPV2195 β-gal− or wildtype FPV. After 40 hours' infection, the cells were labelled with [$^{35}$S]methionine for 4 hours and then lysed with an immunoprecipitation buffer. The F protein present in the lysates of cells infected with the recombinants was immunoprecipitated with a guinea pig polyclonal serum directed against all the proteins of the measles virus, in the presence of Staphylococcus aureus protein A bound to Sepharose. The immunoprecipitated proteins were analyzed on polyacrylamide gel in the presence of SDS; the dried gel was subjected to autoradiography. The results shown (FIG. 4) for the recombinant FPV3113 demonstrate the presence of the primary translation product of the mRNA corresponding to the F gene (F°), as well as the cleavage products $F_1$ and $F_2$.

REFERENCES

Brown, T. D. K. Span 28, 68–70 (1985).

Chakrabarti, S., Robert-Guroff, M., Wong-Staal, F., Gallo, R. C. and Moss, B. Nature 320, 535–540 (1986).

Drillien, R., Spehner, D., Villeval, D. and Lecocq, J. P. Virology 160, in press (1987).

Hall, C. V., Jacob, P. E., Ringold, G. M. and Lee, F. J. Mol Appl. Gen. 2, 101–109 (1983).

Hu, S. L., Kosowski, S. G. and Dabrymple, J. M. Nature 320, 537–540 (1986).

Kieny, M. P. Lathe, R. and Lecocq, J. P. Gene 26, 91–99 (1983).

Kieny, M. P., Lathe, R., Drillien, R., Spehner, D., Skory, S., Schmitt, D., Wiktor, T., Koprowski, H. and Lecocq, J. P. Nature 312, 163–166 (1984).

Kieny, M. P., Rautmann, G., Schmitt, D., Dott, K., Wain-Hobson, S., Alizon, M., Girard, M., Charmaret, S., Laurent, A., Montagnier, L. and Lecocq, J. P. Biotechnology 4, 790–795 (1986).

Lathe, R., Vilotte, J. L. and Clark, A. J. Gene in press (1987).

Mackett, M., Smith, G. L. and Moss, B. PNAS U.S.A. 79, 7415–7419 (1982).

Moss, V., In "Virology" (Ed. B. N. Fields) pp. 685–703 Raven Press, New York (1985).

Panicali, D., Davis, S. W., Weinberg, R. L., Paoletti, E. Proc. Natl. Acad. Sci. USA 80, 5364–5368 (1983).

Sam, C. K. and Dumbell, K. R. Ann. Virol. (Inst. Pasteur) 132, 135–150 (1981).

Smith, G. L., Mackett, M., Moss, V. Nature 302, 490–495 (1983).

Taylor, J., Weinberg, R., Desmettre, P., Paoletti, E. In: Modern approaches to new vaccines including preventing of AIDS. Cold Spring Harbor, New York.

Abstracts of the 1987 meeting (9–13 September) pp. 120.

We claim:

1. A recombinant fowlpox virus, the genome of which comprises a DNA fragment encoding a polypeptide which is heterologous to the fowlpox virus, under the control of appropriate elements providing for its expression in a cell infected with said recombinant fowlpox virus; said DNA fragment being inserted between ORF7 and the 32-bp noncoding intergenic region upstream of ORF9.

2. The recombinant fowlpox virus according to claim 1, which is attenuated.

* * * * *